United States Patent [19]

Erdman et al.

[11] Patent Number: 5,227,303
[45] Date of Patent: Jul. 13, 1993

[54] SAMPLE DISSOLUTION CHAMBER

[75] Inventors: George R. Erdman, Harrisonburg; Douglas C. Fischer, Shenandoah, both of Va.

[73] Assignee: Merck & Co., Inc., Rahway, N.J.

[21] Appl. No.: 841,932

[22] Filed: Feb. 25, 1992

[51] Int. Cl.$^5$ ............................................. C12M 1/28
[52] U.S. Cl. .................................. 435/291; 435/287; 435/292; 435/294; 435/31; 436/179; 436/180; 422/99
[58] Field of Search .................. 422/99, 100; 436/179, 436/180, 174; 435/291, 31, 292, 293, 294

[56]  References Cited
U.S. PATENT DOCUMENTS

| | | | |
|---|---|---|---|
| 4,036,698 | 7/1977 | Bush et al. | 195/103.5 |
| 4,351,900 | 9/1982 | Lemonnier | 435/292 X |
| 4,397,945 | 8/1983 | Lemonnier | 435/292 X |
| 4,640,777 | 2/1987 | Lemonnier | 210/433.2 |
| 4,863,868 | 9/1989 | Holley | 435/294 |

*Primary Examiner*—Jill A. Johnston
*Assistant Examiner*—Long V. Le
*Attorney, Agent, or Firm*—Charles M. Caruso

[57] ABSTRACT

There is disclosed an automated system for testing the sterility of products intended for human health administration or for human consumption. The system permits a plurality of samples of a product to be concurrently tested. To accomplish this, the system includes a novel apparatus for thoroughly mixing therein a plurality of product samples to assure that a statistically meaningful representation of product samples are subjected to sterility testing. The system is arranged so that multiple samples of a product to be tested are deposited in the mixing apparatus after which the mixed samples are conveyed to testing canisters along with appropriate growth media to determine that the product is sterile or that the product is free from microbial contamination.

5 Claims, 4 Drawing Sheets

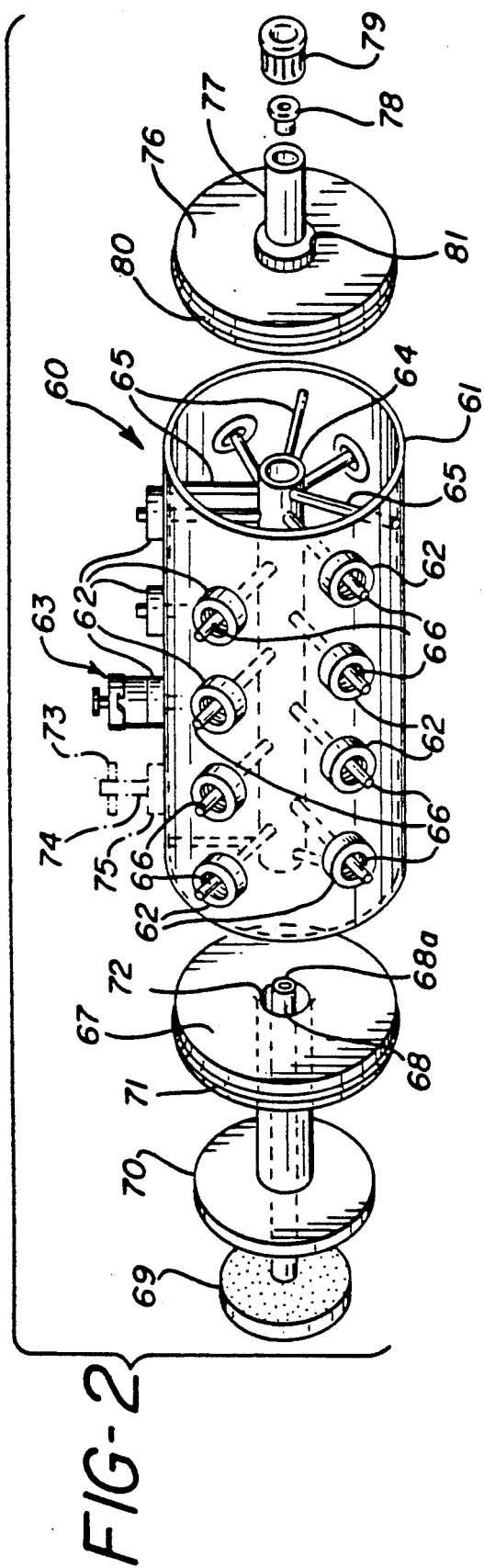
FIG-2
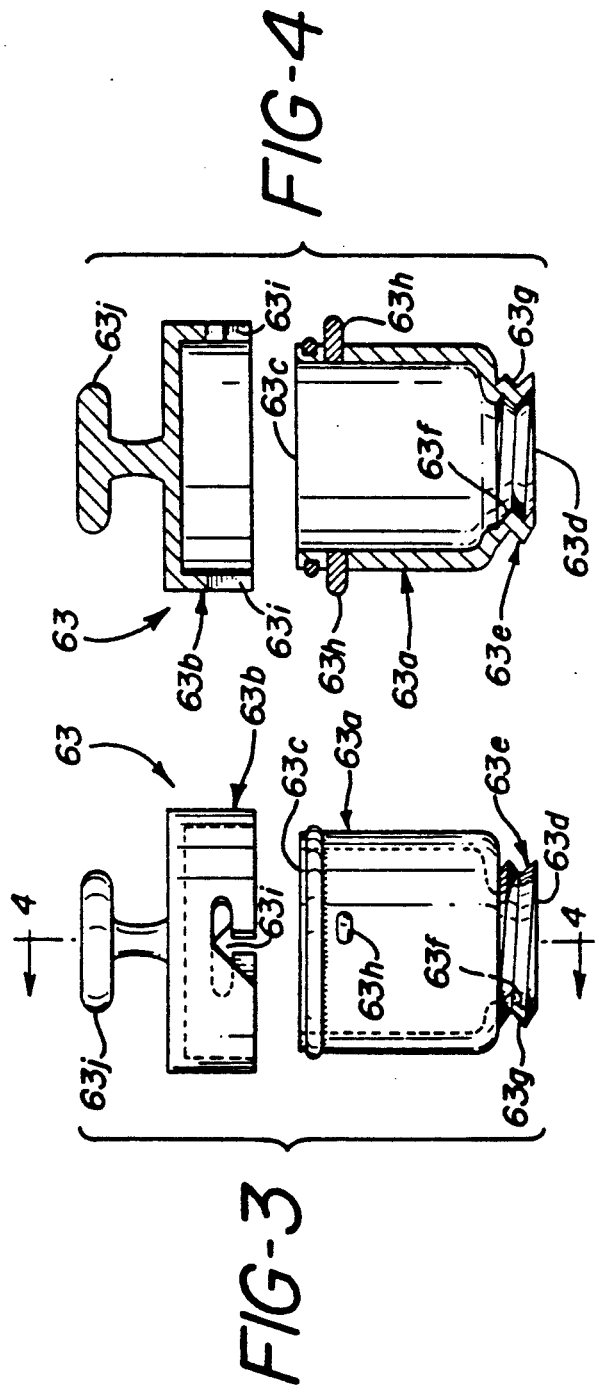
FIG-3
FIG-4

SAMPLE DISSOLUTION CHAMBER

BACKGROUND OF THE INVENTION

In the pharmaceutical and food industries, there is a need to establish that products intended for human health administration or for human consumption are sterile or free from microbial contamination to assure that they are acceptable for their intended uses. Methods and apparatus currently employed for these purposes typically involve withdrawing a sample of a product from its container using a syringe. If the product to be tested is in solid form such as a powder, discrete particles, and the like, a sterile liquid is first injected into the container to suspend or dissolve the product before it is withdrawn for testing. Generally, multiple product samples are individually collected from separate containers and placed in a separate sterile vessel to which additional sterile liquid may be added as needed. This method of sterility testing requires numerous manipulations, each of which increases the risk of contaminating the samples regardless of the care taken in performing each manipulation.

It is inherent in these types of sterility testing that microbes are introduced during the test which may not be distinguishable from those that may be present in the product being tested. Such microbial contamination can be introduced into the product by the environment in which the test is conducted, the test equipment utilized and the personnel performing the tests. A test result is considered to be "false positive" when it reveals the presence of contaminating microbes when none, in fact, are present in the product being tested. Using currently accepted methods and apparatus to conduct sterility testing can result in obtaining "false positive" readings which can translate into significant loss of labor, time, effort and product.

SUMMARY OF THE INVENTION

It has now been found that the shortcomings of the methods currently followed in conducting sterility product testing are overcome by the automated sterility testing system of the invention.

In general, the automated sterility testing system of the invention comprises: means for concurrently mixing, dissolving or diluting a plurality of samples of a product to be tested for sterility; means for conveying a diluent or solvent from a supply source to said mixing, dissolving or diluting means and to test canisters and control canisters; means for conveying growth control media from a supply source to said control canisters and said test canisters; means for conveying said plurality of product samples from said mixing, dissolving or diluting means through said test canisters; and means for incubating said plurality of product samples in said test canisters and said growth control media in said control canisters.

The sterility testing system of the invention automatically and concurrently supplies a plurality of product samples to the mixing, dissolving or diluting means and automatically supplies diluent or solvent to the mixing, dissolving or diluting means. In addition, the system includes means for supplying growth control media to test canisters containing the plurality of product samples to be tested as well as to control canisters against which sterility of the product samples in the test canisters is determined, after incubation, by the presence or absence of microbial contamination.

The mixing, dissolving or diluting means employed in the system of the invention is a novel sample dissolation chamber that comprises a generally cylindrical, hollow body having a plurality of bosses spaced about its circumferential surface adapted to receive containers of product. Means are provided within the body of the chamber for penetrating the product containers to extract some or all of the product from the containers into the body of the chamber. The chamber is provided with means to receive a supply of solvent or diluent in order to dilute or dissolve the product samples as required and with means to convey the product samples to test canisters. The novel sample dissolution chamber is also equipped with agitation means to assure complete dilution or dissolution of the product samples and with means to vent air from within the chamber.

Where the system of the invention utilizes flexible tubing to convey the various liquids and fluids (e.g., product samples, diluents, solvents, growth media and the like) through it, a novel pinch valve is employed to control the flow of fluids and liquids through the system. The novel pinch valve of the invention generally comprises a body having a passage adapted to permit a section of flexible tubing to be threaded through it; a cylindrical cam member rotatably mounted at one end to said body with the other end of said cam member positioned above said passage; and, means to rotate said cam member from a non-impinging open position to an impinging closed position with respect to a section of flexible tubing contained in said passage. Thus, when the cam member is in its non-impinging open position, fluids or liquids are permitted to pass freely through the flexible tubing. As the cam member is rotated toward its impinging, closed position, it impinges upon the flexible tubing to restrict or stop the flow of liquids or fluids through it depending upon the degree to which the cam member is rotated toward its impinging, closed position. The novel pinch valve of the invention also includes associated means to adjust the gap dimension of the passage and thereby accommodate flexible tubing having different diameters.

DETAILED DESCRIPTION OF THE INVENTION

The automated sterility testing system of the invention and the novel apparatus used in conjunction with it will become more apparent from the ensuing description when considered together with the accompanying drawing wherein like reference numerals denote like parts and wherein:

FIG. 2 is a perspective view, partially exploded and part in phantom, of the novel sample dissolution chamber of the invention;

FIG. 3 is an exploded elevation view of one type of sample cup that can be used with the sample dissolution chamber of FIG. 2;

FIG. 4 is a sectional view taken substantially on the line 4—4 of FIG. 3;

Figure 1:
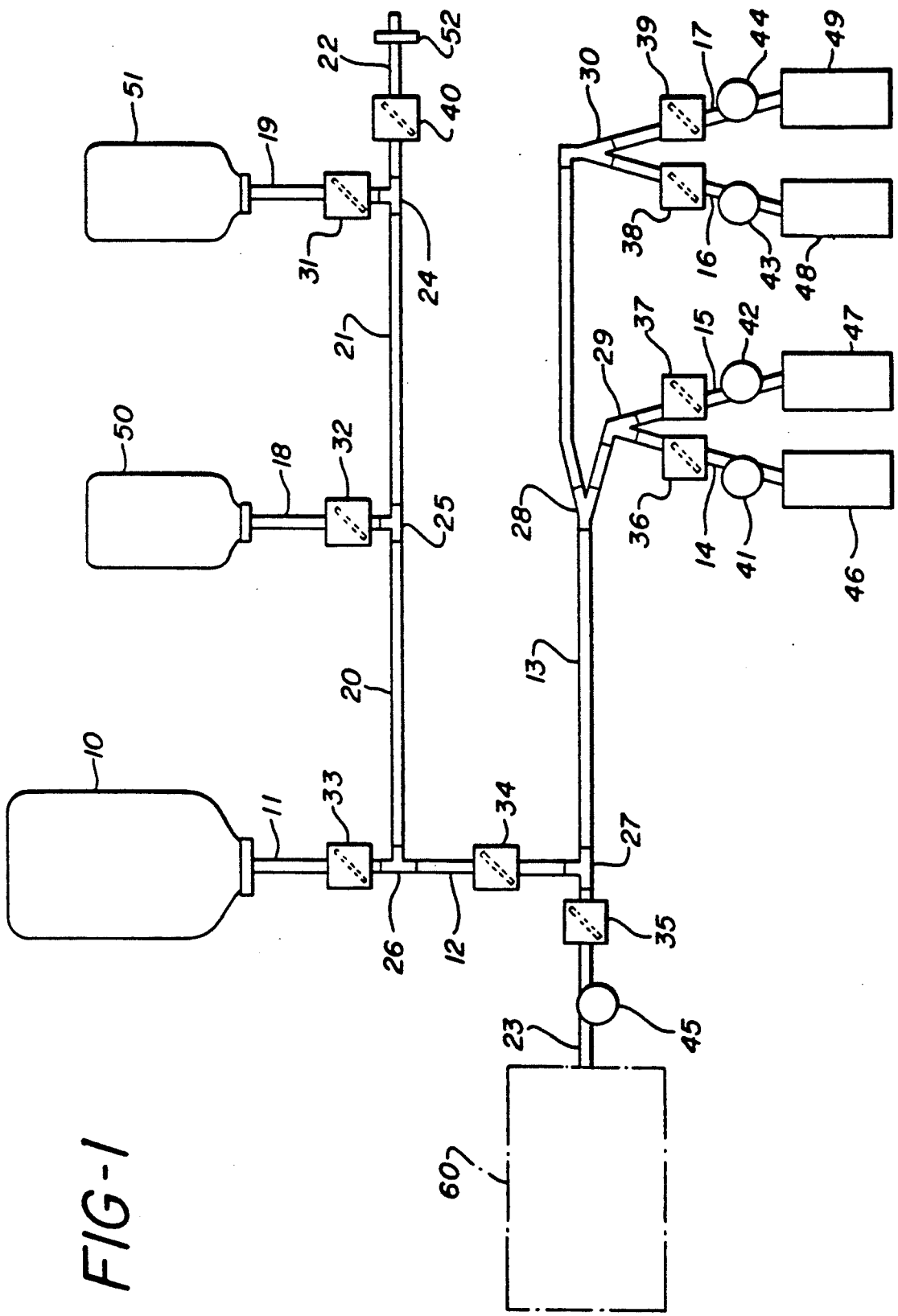
FIG. 1 is a diagrammatic illustration of the system of the invention which incorporates the novel sample dissolution chamber of the invention.

As diagrammatically illustrated in FIG. 1, the automated sterility testing apparatus and system of the invention comprises:

(a) a supply source or reservoir 10 for providing diluent or solvent as required;

(b) a plurality of conduit sections 11, 12, 13, 14, 15, 16, 17, 18, 19, 20, 21, 22 and 23 for conveying air and the liquids to be used;

(c) a plurality of Y connectors 24, 25, 26, 27, 28, 29 and 30 joining various conduit sections;

(d) a plurality of two-way valves 31, 32, 33, 34, 35, 36, 37, 38, 39 and 40 to direct the flow of air and the various liquids used;

(e) a plurality of peristaltic pumps 41, 42, 43, 44, 45 and an air vent 52 to control the flow of the air and liquids;

(f) test canisters 46, 47 in which samples of the product to be tested are placed and culture media is added to verify the sterility of the product samples being tested;

(g) control canisters 48, 49 in which a growth control media is placed to validate the sterility of the conduits, diluent and growth control media being used;

(h) a supply source such as containers 50, 51 for the growth media to be used in the test; and, (i) the sample dissolution chamber of the invention 60 which is described in more detail hereinbelow.

Except for the dissolution chamber of the invention 60, the various components of the system identified in FIG. 1 are all commercially available items which are readily obtainable. For example, the conduit sections, Y-valves, two-way valves, peristaltic pumps and the test and control canisters can be commercially obtained from the Millipore Corporation and details of their construction and use are disclosed in U.S. Pat. Nos. 4,036,698 and 4,640,777.

The sterile diluent or solvent and the growth media used are also commercially available from such suppliers as Abbott Laboratories, Becton Dickinson, and Adams Laboratories.

While rigid conduit sections can be used in the invention system, flexible tubing is preferred as it is less costly and easier to handle. When flexible tubing is used, it is also preferred to use the novel pinch valves of the invention in place of commercially available two-way valves. These novel pinch valves are described in more detail hereinbelow.

With reference to the system diagrammatically shown in FIG. 1, testing the sterility of a product by the process of the invention comprises first sterilizing the sample dissolution chamber 60 such as by autoclaving and allowing the steam to condense and collect in the chamber 60 as distilled water which is then used as later described.

Depending upon whether the product sample to be tested is a liquid or solid (e.g., a product in the form of granules, particulates or a powder) a suitable solvent or diluent for the product sample is gravity fed from supply source or reservoir 10 through conduit 11 and is then directed by Y connector 26 through conduit 12, by Y connector 27 through conduit 13, by Y connectors 28, 29 through conduits 14, 15 to test canisters 46, 47 and also by Y connector 30, through conduits 16, 17 to control canisters 48, 49. During testing, two-way valves 31, 32, 33, 34, 35, 36, 37, 38, 39 and 40 are set to direct the flow of air or liquids from a source to a particular destination. In this instance, the solvent or diluent is directed from supply source or reservoir 10 to test canisters 46, 47 and to control canisters 48, 49 and the two-way valves are set accordingly.

The solvent or diluent serves to wet the membranes or filters (not shown) which are provided in the bottoms and form a part of each of the test canisters 46, 47 and control canisters 48, 49. This wetting action reduces and minimizes any tendency that the product sample to be tested may have to bind or adhere to the membrane or filter.

Distilled water from the sample dissolution chamber 60 is then supplied by means of peristaltic pumps 43, 44 through conduit 23 directed by Y connector 27 through conduit 13 and directed by Y connectors 28, 30 through conduits 16, 17 to control canisters 48, 49 to assure that these components of the system, as well as the diluent or solvent previously supplied to control canisters 48, 49 are all sterile.

One or more growth mediums from the growth media supply or containers 50, 51 is then pulled by means of peristaltic pumps 43, 44 through conduits 18, 19, 20, 21 and Y connectors 24, 25 to Y connector 26 through conduit 12 and directed by Y connector 27 through conduit 13 and by Y connectors 28, 30 through conduits 16, 17 to control canisters 48, 49. These portions of the system; i.e., conduits 20, 21, 22, 12, 13, 16, 17 and Y connectors 24, 25, 26, 27, 28, 30 are purged by drawing air through them from air vent 52 using peristaltic pumps 43, 44.

The tops of each of the commercially obtained control canisters 48, 49 are equipped with a sterilizing filter and a vent port (neither being shown) and purging air is vented from the control canisters 48, 49 to the atmosphere through these ports and filters. The bottoms of the control canisters 48, 49 are then closed and conduits 16, 17 are sealed and cut. The thusly closed and sealed control canisters 48, 49 are then removed from the system and placed in an incubator.

A plurality of samples from the product to be tested are attached to the sample dissolution chamber 60. An amount of diluent or solvent sufficient to dilute or dissolve the product samples, depending upon the nature and the physical form of the product samples, is pumped into the sample dissolution chamber 60 by peristaltic pump 45 from reservoir 10 through conduits 11, 12, 23 directed by Y connectors 26, 27. The diluent or solvent and the product samples are then thoroughly mixed in the sample dissolution chamber 60 as described more fully hereinafter.

The thusly dissolved or diluted product samples are then delivered to test canisters 46, 47 via conduit 23 directed by Y connector 27 through conduit 13 and directed by Y connectors 28, 29 through conduits 14, 15 to test canisters 46, 47. Peristaltic pumps 41, 42 are used to assure that equal amounts of product sample are delivered to each of the test canisters 46, 47. When delivered to test canisters 46, 47, the product sample passes through the membranes or filters in the bottoms of the test canisters which serve to retain any residual contaminating organisms that may have been present in the product sample.

Where the product sample subjected to this sterility test is one having bacteriostatic properties such as an antibiotic, it is preferred that conduits 16, 17 and 23 be disengaged from the system and connected to a suitable receptacle (not shown). These components as well as conduit 13 and Y connectors 27, 28, 29, 30 are then rinsed with diluent or solvent from reservoir 10 to assure that any residual product sample that may be present is removed from these components of the system.

Where the product sample to be tested is one that does not have bacteriostatic properties such as sodium bicarbonate, the rinsing step described above need not be included in the testing process.

The test canisters 46, 47 and the membranes or filters in their bottoms are then rinsed with diluent or solvent pulled from reservoir 10 through conduit 11 directed by Y connector 26 through conduit 12, by Y connector 27 through conduit 13 and directed by Y connector 28, 29 through conduits 14, 15 to test canisters 46, 47 using peristaltic pumps 41, 42. This serves to remove any residual product sample that may be present in these components.

One or more growth mediums from the growth media supply or container 50, 51 is then pulled by means of peristaltic pumps 41, 42 through conduits 18, 19, 20, 21 and Y connectors 24, 25 to Y connector 26 through conduit 12 then directed by Y connector through conduit 13 and by Y connectors 28, 29 through conduits 14, 15 to test canisters 46, 47. These components of the system (i.e., conduits 20, 21, 22, 12, 13, 16, 17 and Y connectors 24, 25, 26, 27, 28, 30) are then purged by drawing air througj them from air vent 52 using peristaltic pumps 41, 42.

The bottoms of test canisters 46, 47 are then closed and inlet conduits 14, 15 are sealed and cut. The closed and sealed test canisters 46, 47 are then removed from the system and placed in an incubator for a period of time and at a temperature sufficient to permit any contaminating organisms that may have been present to grow. If no growth is evident at the end of the incubation period, the product passes the test for sterility.

As shown in FIG. 2, the novel sample dissolution chamber of the invention, generally identified by reference numeral 60, comprises a hollow cylindrical housing or body 61 having a plurality of spaced bosses 62 mounted to its outer circumferential surface. Bosses 62 communicate with the interior of housing or body 61 and are internally threaded to receive and carry sample mounting cups 63. While any number of bosses 62 can be provided on the outer circumference of housing or body 61 and be uniformly or randomly spaced apart, a typical sample dissolation chamber 60 will have about 20 such bosses 62 uniformly spaced about the outer circumferential surface of housing or body 61.

Positioned within the housing or body 61 is a mounting bar 64 which is retained substantially in axial, longitudinal alignment within housing or body 61 by means of a plurality of spacer rods 65 which can be provided adjacent to either or both ends of mounting bar 64. Spacer rods 65 can be secured to mounting bar 64 by any suitable means such as threadably securing the spacer rods 65 into threaded receptacles provided in the mounting bar 64. Spacer rods 65 radiate outwardly from mounting bar 64 and are dimensioned to frictionally engage the inner circumferential surface or wall of housing or body 61 to maintain the mounting bar 64 substantially in alignment with the central, longitudinal axis of housing or body 61.

Secured to the outer circumference of mounting bar 64 and extending along its length are a plurality of spaced pusher rods 66. Pusher rods 66 radiate outwardly from mounting bar 64, are positioned to centrally protrude through bosses 62 and are dimensioned so that their ends extend beyond the upper planar surfaces of bosses 62 an amount sufficient to penetrate the stoppered end of a product container to be tested as described in more detail hereinbelow. Pusher rods 66 can be secured to mounting bar 64 by any suitable means but are preferably secured so that they can be removed such as by threadably securing the pusher rods 66 into threaded receptacles provided in mounting bar 64 in a manner similar to that described above with respect to mounting the spacer rods 65. By providing means to removably secure the pusher rods 66 to the mounting bar 64, pusher rods of different lengths and/or having different end configurations (e.g., needles) can be provided to accommodate the penetration of product containers having different stoppered ends.

One end of housing or body 61 is closed with a vent closure means comprising a circular disc 67; an elongated, hollow vent tube 68; a vent filter 69; and a knob 70. Circular disc 67 is provided with a circumferential groove (not shown) in which there is seated an O-ring 71 that serves to seal that end of housing or body 61 when disc 67 is secured to it. Disc 67 can be secured to housing or body 61 using conventional means such as by providing threaded receptacles in the outer circumferential wall of disc 67 to threadably receive screws or pins through circumferential apertures in the wall of housing or body 61 (not shown). An aperture 72 is formed in the center of disc 67 and is of a size sufficient to accommodate the passage there-through of vent tube 68 so that one end 68a of vent tube 68 extends into and communicates with the interior of housing or body 61. Vent filter 69 is secured to the other end of vent tube 68 and knob 70 is mounted on vent tube 68 intermediate its ends. The vent filter 69 is of the type that permits air to escape through it but not aqueous liquids or moisture; i.e., it is hydrophobic. Such hydrophobic vent filters are preferred as they also prevent contaminants from entering the housing or body 61.

Alternatively, vent filter 69 and vent tube 68 can be threadably mounted directly to the housing or body 61 by providing an additional boss as shown in phantom in FIG. 2 at 13, 14 and 75, respectively identifying the vent filter, vent tube and additional boss.

The other end of housing or body 61 is its discharge end and it is closed with a discharge closure means comprising a circular disc 76, a hollow discharge tube 77, removable elastomeric plug or stopper 78 sized to frictionally engage the inner circumferential wall of hollow discharge tube 77, and a crimped metal cap 79 which holds the plug or stopper 78 in place on the discharge tube 77. Diluent or solvent is delivered to and withdrawn from housing or body 61 by inserting an appropriate needle (not shown) through the elastomeric plug or stopper 78. Circular discharge disc 76 is also provided with a circumferential groove (not shown) in which there is seated an O-ring 80 which serves to seal that end of housing or body 61 when disc 76 is secured to it in the same manner as described above with regard to disc 67. An aperture 81 is formed in the center of discharge disc 76 and serves to provide a communicating passage with the interior of housing or body 61 and hollow discharge tube 77.

As shown in FIGS. 3 and 4, the sample mounting cups 63 which can be used with the sample dissolution chamber 60 of the invention can comprise a cup member 63a and a hollow cap 63b, the cup member 63a being open at both its upper end 63c and its lower end 63d. The neck 63e of lower end 63d is provided with internal and external threads 63f and 63g, respectively. One or more protruding ears 63h are provided adjacent the open upper end 63c of cup member 63a which are inserted into notches 63i provided in cap 63b enabling cap 63b to be secured to the open, upper end 63c of cup 63a similar to a bayonette-type of attachment. For ease of attachment and removal, hollow cap member 63b has a grasping knob 63j. The inside diameter of cap 63b is sized to frictionally engage the outer surface at the open, upper end 63c when securing cap 63b to cup 63a.

Figure 5:
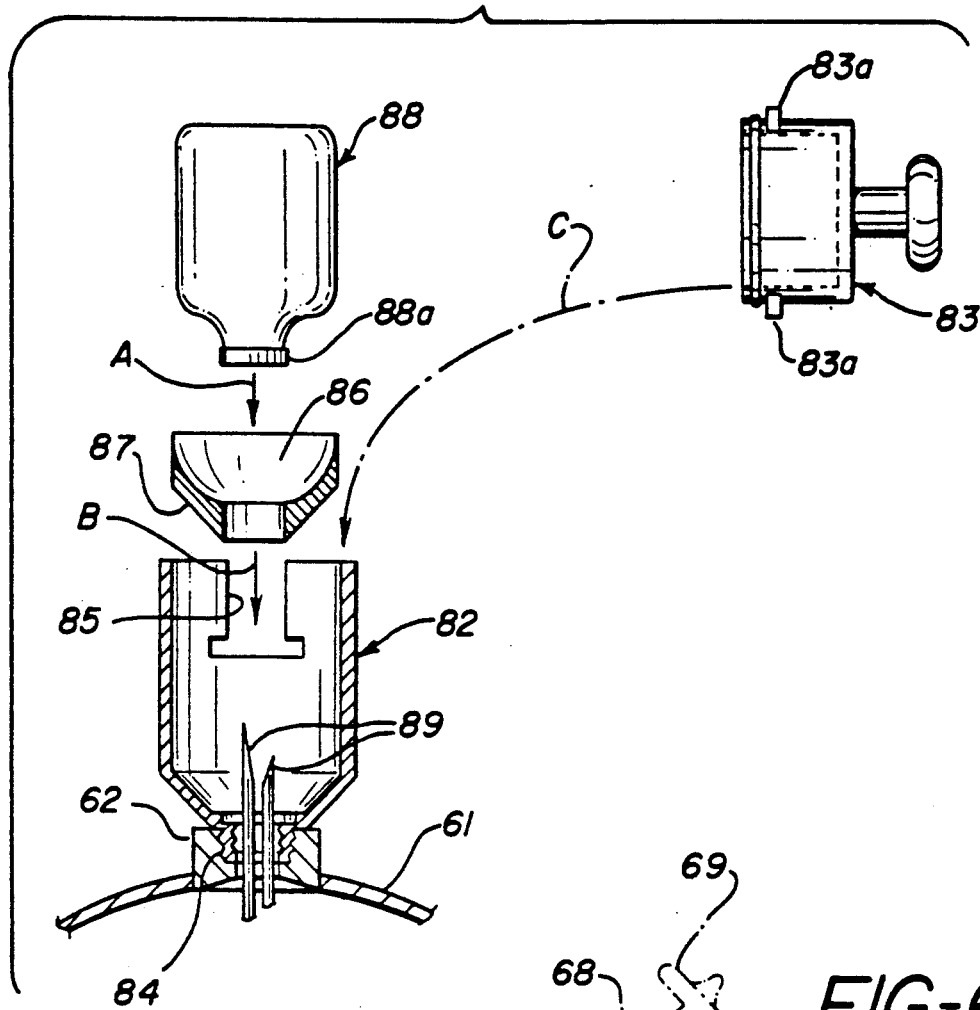
FIG. 5 is an exploded elevation view, part in section, of an adapter that can be used to accommodate product containers of different sizes for use with the sample dissolution chamber of the invention.

One means to accommodate product containers of different sizes for use with the sample dissolution chamber of the invention is illustrated by the adapter means shown in FIG. 5 comprising an adapter cup 82 and hollow cap 83 which are similar to the cup member and hollow cap described in connection with FIGS. 3 and 4 above. As indicated at 84, cup member 82 is threadably secured to a boss 62 of housing or body 61 and has a vertical T-shaped slot 85 formed in its wall. This enables hollow cap 83 to be inserted into adapter cup 82 as indicated by arrow C and then locked in place by engaging protrusions 83a provided on hollow cap 83 with the notches of T-shaped slot 85. The body of the adapter cup 82 is sized to removably receive a product container guide 86 which is the form of a truncated hollow cylinder having a tapered, frustoconical end 87. A typical product container which can not be threadably secured to a boss 62 of housing or body 61 is identified by reference numeral 88.

To secure product container 88 to the housing or body 61, adapter cup 82 is first threadably secured to boss 62 as indicated at 84. Product container 88 is then slidably inserted into and seated in container guide 86 as indicated by arrow A so that its stoppered end 88a protrudes from the frustoconical end 87 of the container guide 86. Next, the assembled container guide 86 and product container 88 are slidably inserted into adapter cup 82 as indicated by arrow B and guided by the walls of adapter cup 82 until the stoppered end 88a of product container 88 is penetrated by appropriate penetrating means such as needles 89 secured to mounting bar 64 in place of pusher rods 66 (see FIG. 2). Diluent or solvent from housing or body 61 can then be delivered into the product container 88 through needles 89 to dissolve or dilute the product. Product sample can then be extracted from the product container 88 through needles 89 for delivery into the housing or body 61.

Figure 6:
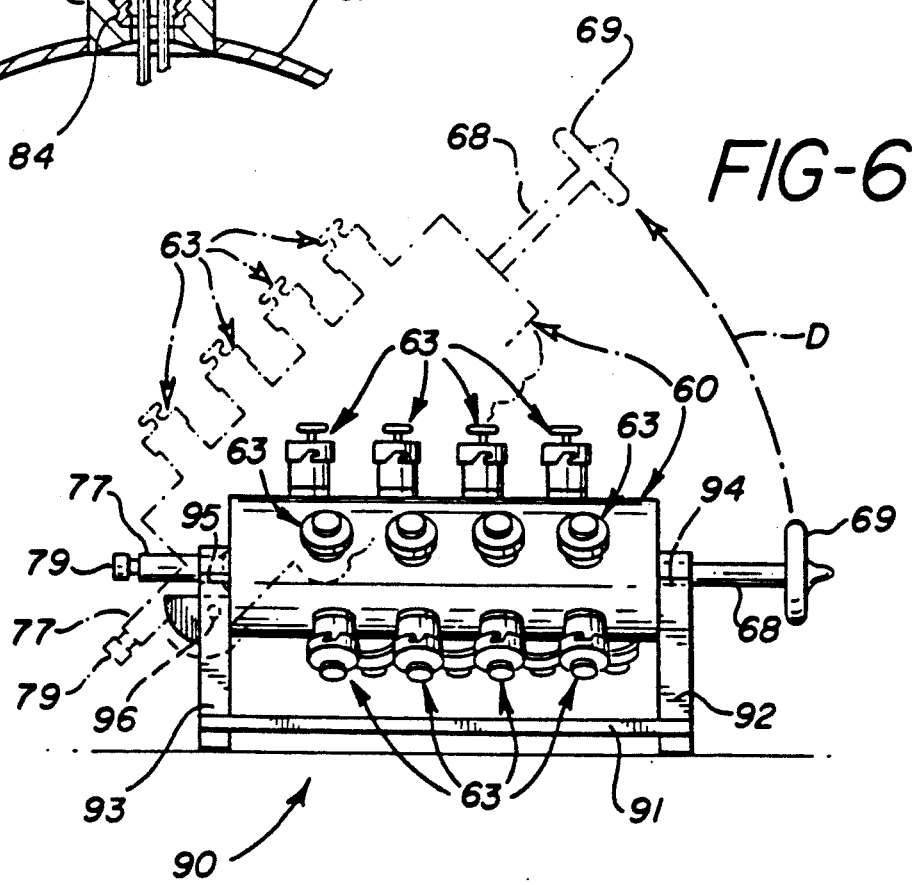
FIG. 6 is a side elevation view of the sample dissolution chamber of the invention shown seated in a suitable cradle that permits rotation of the sample dissolution chamber as shown in phantom.

After samples of product have been extracted from their containers into the sample dissolution chamber, it is preferred that the samples be thoroughly mixed to assure that they are completely dissolved or sufficiently diluted before being withdrawn from the sample dissolution chamber for sterility testing. One means by which this mixing can be accomplished is illustrated in FIG. 6 in the form of a U-shaped cradle, generally identified by reference numeral 90, having a base 91 interconnecting opposed walls 92, 93. A slot or groove 94 and 95 is formed in the upper ends of each wall 92, 93 to seat therein at one end vent tube 68 and, at the other end, discharge tube 77 so that the sample dissolution chamber 60 is normally horizontally disposed during attachment of product containers and extracting product sample from them. End wall 93 in which discharge tube 77 is seated is provided with a pivot assemblage 96 that enables the sample dissolution chamber 60 to be rotated in the direction of arrow D to an angular position as shown in phantom. By rotating the sample dissolution chamber 60 several times in this manner, thorough mixing is assured of the product samples contained therein.

Figure 7:
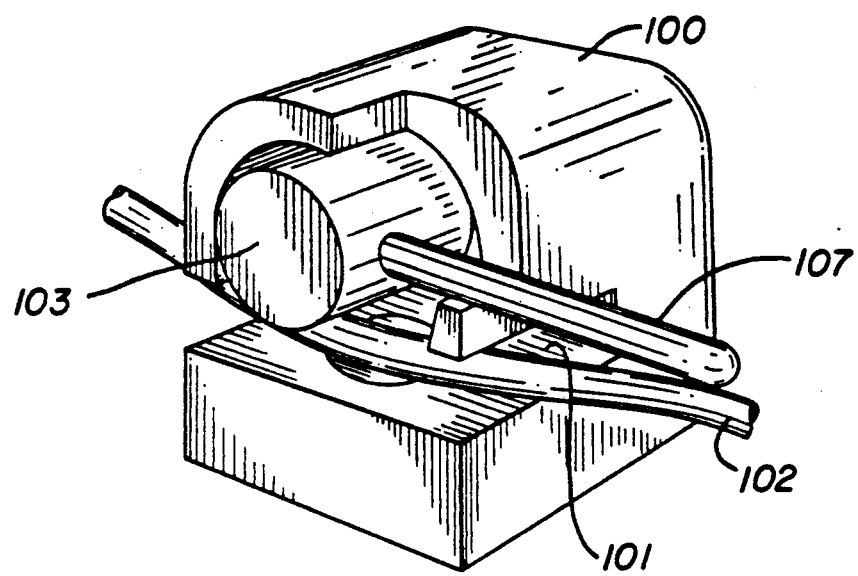
FIG. 7 is a perspective view of the novel pinch valve of the invention.
Figure 8:
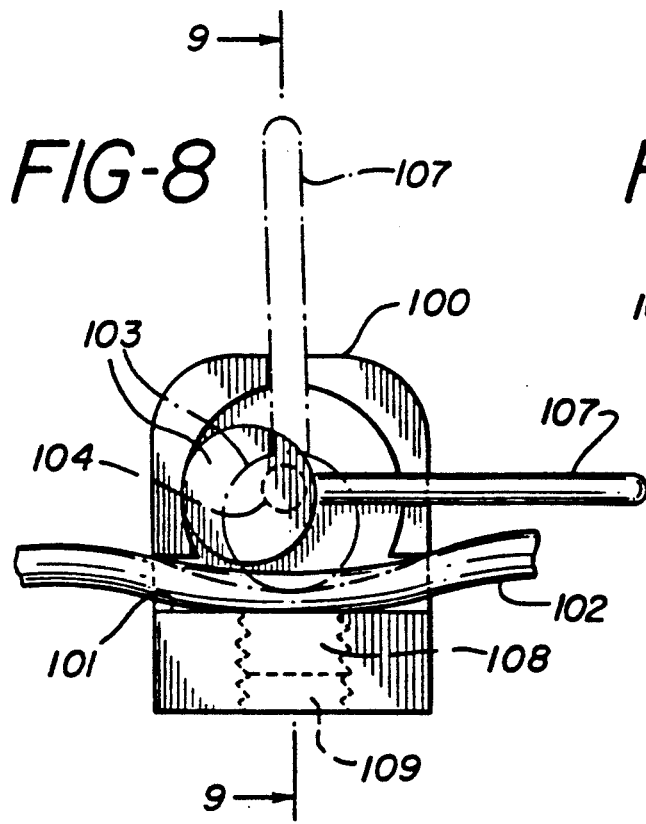
FIG. 8 is a front elevation view of the pinch valve shown in FIG. 7.
Figure 9:
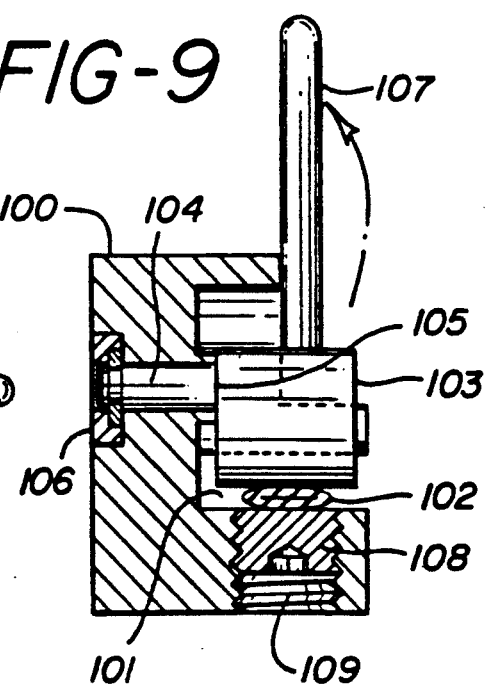
FIG. 9 is a view taken substantially in the direction of line 9—9 of FIG. 8.

As described earlier, where the system of the invention utilizes flexible tubing to convey the various liquids and fluids employed, it is preferred that the novel pinch valve of the invention shown in FIGS. 7-9 be incorporated into the system to control the flow of the liquids and fluids.

As can be seen in FIGS. 7-9, the novel pinch valve of the invention comprises a body 100 having a transverse passage 101 formed in it through which a section of flexible tubing 102 can be threaded. The inner end of a cylindrical cam member 103 is rotatably mounted to the body 100 by means of axle 104, one end of which is secured to but off-set from the center of cam member 103 at 105 and the other end of which is rotatably seated in a retaining member 106. A handle 107 is secured to cam member 103 adjacent its outer end. When handle 107 is in a substantially horizontal position, as shown in solid lines in FIG. 8, flexible tubing 102 is not constricted permitting fluids or liquids to be freely conveyed through it. As shown in phantom in FIGS. 8 and 9, when the handle 107 is moved to a vertical position, it rotates cam member 103 to impinge upon and collapse flexible tubing 102 thereby stopping the flow of fluids or liquids being conveyed through it.

The rate of flow of fluids and liquids through flexible tubing 102 can also be controlled by rotating handle 107 through any number of positions intermediate its fully open horizontal position and its fully closed vertical position to increase or decrease the degree to which cam member 103 impinges upon flexible tubing 102.

To accommodate flexible tubing of different diameters, an adjusting screw 108 can be positioned in body 100 beneath passage 101 and access to adjusting screw 108 can be done through port 109. By raising or lowering adjusting screw 108, the height of passage 101 can be increased or decreased to closely accept flexible tubing having different diameters.

While the invention has been described in some detail and with particularity, it should be understood and will become apparent to those skilled in this art that changes and modifications can be made therein without departing from the scope and spirit of the invention recited in the claims.

What is claimed is:

1. A sample dissolution chamber for thoroughly mixing and diluting or dissolving a plurality of samples of a product to be tested for microbial contamination, said sample dissolution chamber comprising:
   (a) a hollow, cylindrical housing or body having inner and outer circumferential surfaces, a vent end and a discharge end;
   (b) a plurality of spaced bosses mounted on said outer circumferential surface and communicating with said hollow interior of said housing or body, said bosses extending outwardly from said outer circumferential surface such that upper planar surfaces of said bosses are spaced from said outer circumferential surface and having means for removably securing thereto a plurality of sample mounting cups;

(c) a plurality of pusher rods having inner and outer ends and means for mounting said plurality of pusher rods within said housing or body to radiate outwardly from said housing or body and centrally protrude through said bosses so that said outer ends of said pusher rods extend beyond the upper planar surfaces of said bosses;

(d) a vent closure means removably secured to and sealing the vent end of said housing or body, said vent closure means including a hollow vent tube communicating with the interior of said housing or body; and, (e) a discharge closure means removably secured to and sealing the discharge end of said housing or body, said discharge closure means including a hollow discharge tube communicating with the interior of said housing or body.

2. The sample dissolution chamber of claim 1 wherein said sample mounting cups individually comprise a hollow, cylindrical cup member having a neck at one end which is provided with means for removably securing said cup member to said bosses; a hollow cap member having means for removably securing said hollow cap member to said cup member, said cup member and said hollow cap member being of a size to accommodate therein containers of product to be tested for microbial contamination.

3. The sample dissolution chamber of claim 2 wherein said cup member has an external diameter and said hollow cap member has an internal diameter which is sized to be removably secured over said external diameter of said cup member, said cup member includes a product container guide removably seated therein to accommodate product containers of different sizes.

4. The sample dissolution chamber of claim 3 wherein said product container guide comprises a truncated, hollow cylindrical member having an upper end of uniform diameter and a tapered frustoconical lower end enabling product containers of different sizes to be inserted into said container guide and said container guide with said product container together to be slidably inserted into and seated within said cup member.

5. The sample dissolution chamber of claim 1 wherein means for mounting said pusher rods within said housing or body comprises an elongated mounting bar disposed within said housing or body; a plurality of spacer rods having inner and outer ends, the inner ends of which are secured to at least one end of said mounting bar and radiating outwardly therefrom so that the outer ends of said spacer rods frictionally engage the inner circumferential surface of said housing or body to retain said mounting bar substantially in axial, longitudinal alignment within said housing or body; and, means on said mounting bar for removably securing thereto said pusher rods.

* * * * *